United States Patent [19]
Shimazaki et al.

[11] Patent Number: 5,264,438
[45] Date of Patent: Nov. 23, 1993

[54] QUINAZOLINE DERIVATIVES

[75] Inventors: Norihiko Shimazaki; Hitoshi Yamazaki; Takumi Yatabe, all of Tsukuba; Hirokazu Tanaka, Tsuchiura; Yoshikuni Itoh, Tsukuba; Masashi Hashimoto, Tokyo, all of Japan

[73] Assignee: Fujisawa Pharmaceutical Co., Ltd., Osaka, Japan

[21] Appl. No.: 627,417

[22] Filed: Dec. 14, 1990

[30] Foreign Application Priority Data

Jan. 2, 1990 [GB] United Kingdom ............... 9000014
Nov. 19, 1990 [GB] United Kingdom ............... 9025065

[51] Int. Cl.$^5$ .................. A61K 31/505; C07D 401/06; C07D 413/14
[52] U.S. Cl. .................. 514/259; 514/232.5; 514/234.5; 544/116; 544/284
[58] Field of Search .............. 544/284, 285, 288, 116; 514/259, 232.5, 234.5

[56] References Cited

U.S. PATENT DOCUMENTS 3,274,194  9/1966  Hayao ................................. 544/285
4,684,654  8/1987  Wright, Jr. et al. ................ 514/259

OTHER PUBLICATIONS

Chemical Abstracts, vol. 111, No. 21, Nov. 20, 1989, Columbus, Ohio, USA Cohen et al "Lack of a difference between ketanserin and ritanserin in Central vs. peripheral serotonin receptor antagonism" p. 70, Column 2, abstract No. 187 437y & Life Sci. 1989, 45(13), 1185-9.

Chemical Abstracts, vol. 110, No. 13, Mar. 27, 1989, Columbus, Ohio, USA S. Heptinstall, J. Bevan "How can we inhibit 5-HT-in-duced platelet aggregation and why should we bother?" p. 46, column 1, abstract No. 107 881e & Folia Haematol. (Leipzig) 1988, 115(4), 475-8.

Chemical Abstracts, vol. 101, No. 15, Oct. 8, 1984, Columbus, Ohio, USA A. Nevelsteen et al. "Restoration of post-thrombotic peripheral collateral circulation in the cat by ketanserin, a selective 5-HT2-receptor antagonist" p. 38, column 1, abstract-No. 122 772c & Arch Int. Pharmacodyn. Ther. 1984, 270(2), 268-79.

Primary Examiner—Mukund J. Shah
Assistant Examiner—Y. N. Gupta
Attorney, Agent, or Firm—Oblon, Spivak, McClelland, Maier & Neustadt

[57]  ABSTRACT

Compounds of the formula:

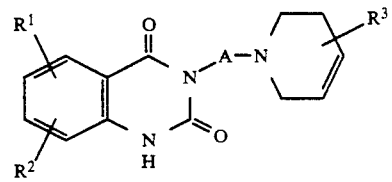

are described wherein $R^1$, $R^2$, $R^3$ and A are described in the claims. These compounds show significant dopamine receptor agonist activity.

13 Claims, No Drawings

QUINAZOLINE DERIVATIVES

The present invention relates to novel quinazoline derivatives and pharmaceutically acceptable salts thereof.

More particularly, it relates to novel quinazoline derivatives and pharmaceutically acceptable salts thereof, which display effects on the peripheral or central nervous system, to processes for the preparation thereof, to a pharmaceutical composition comprising the same, to a use of the same as a medicament and to a method of the therapeutic treatment of diseases in a human being or animal.

Accordingly, one object of the present invention is to provide novel quinazoline derivatives and pharmaceutically acceptable salts thereof, which display effects on the peripheral or central nervous system, in particular on the peripheral nervous system.

Another object of the present invention is to provide processes for the preparation of novel quinazoline derivatives and salts thereof.

A further object of the present invention is to provide a pharmaceutical composition comprising, as an active ingredient, said quinazoline derivatives and pharmaceutically acceptable salts thereof.

Still further object of the present invention is to provide a use of said quinazoline derivatives and pharmaceutically acceptable salts thereof as a dopamine receptor agonist, 5-HT receptor antagonist, especially 5-$HT_2$ receptor antagonist; $a_1$ receptor antagonist; and the like and a method of the therapeutic treatment of dopamine receptor; 5-HT receptor, especially 5-HT receptor; $a_1$-receptor mediated diseases, particularly hypertension, cardiovascular disorder (e.g. angina pectoris, myocardial infarction, etc.), Parkinsonism, and the like, in a human being or animal.

The object quinazoline derivatives are novel and can be represented by the following general formula:

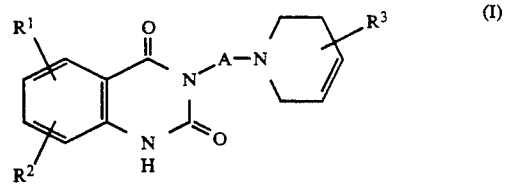

in which
$R^1$ and $R^2$ are each hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl,
$R^3$ is aryl which may have suitable substituent(s), and
A is lower alkylene, and pharmaceutically acceptable salts thereof.

Suitable salts of the object compound (I) are pharmaceutically acceptable, conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, fumarate, methanesulfonate, benzenesulfonate, etc.); a salt with a basic or acidic amino acid (e.g. arginine, aspartic acid, glutamic acid, etc.); and the like.

According to the present invention, the object compound (I) or pharmaceutically acceptable salts thereof can be prepared by the processes as illustrated by the following reaction schemes.

Process 1:

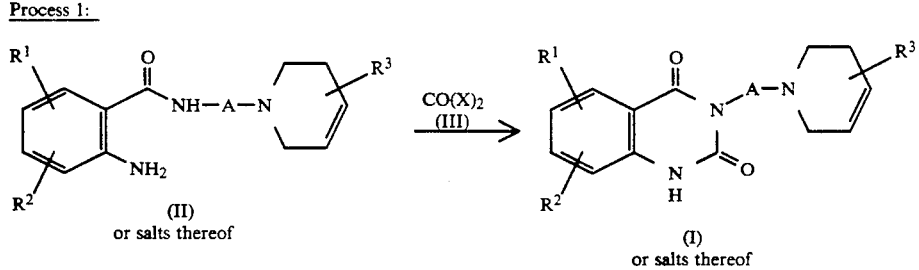

Process 2:

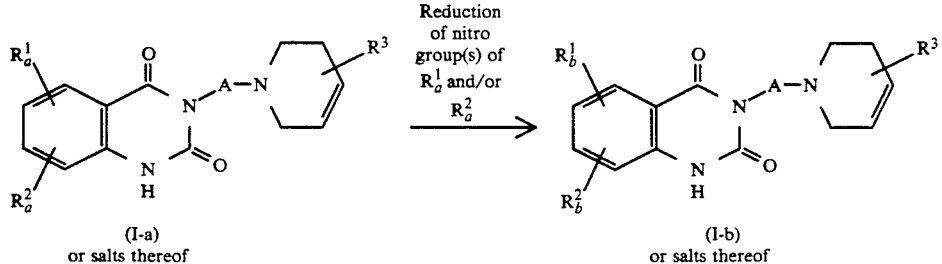

Process 3:

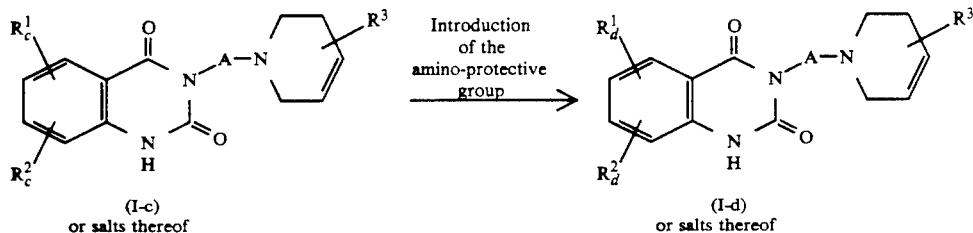

(I-c) or salts thereof

Introduction of the amino-protective group (I-d) or salts thereof

Process 4:

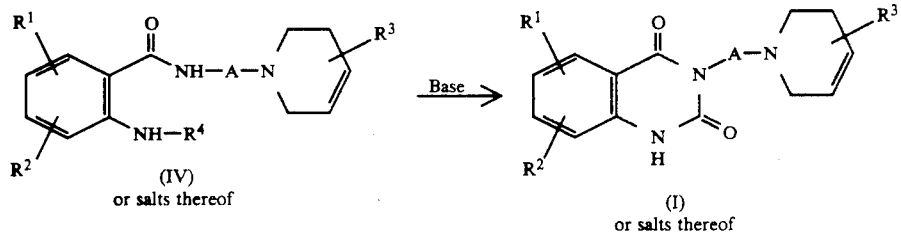

(IV) or salts thereof

Base →

(I) or salts thereof

Process 5:

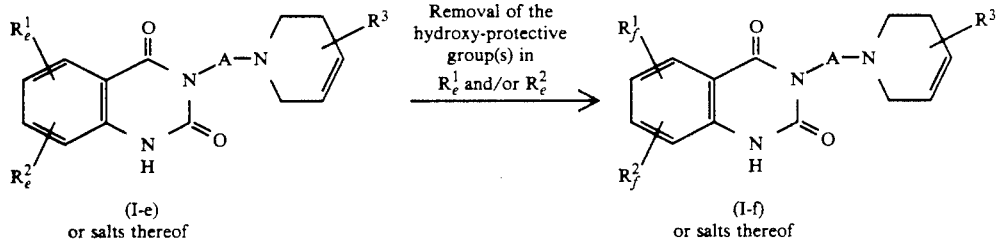

(I-e) or salts thereof

Removal of the hydroxy-protective group(s) in $R_e^1$ and/or $R_e^2$ (I-f) or salts thereof Process 6:

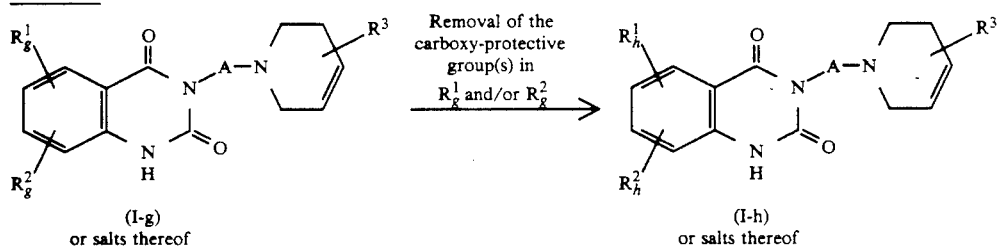

(I-g) or salts thereof

Removal of the carboxy-protective group(s) in $R_g^1$ and/or $R_g^2$ (I-h) or salts thereof wherein
$R^1$, $R^2$, $R^3$ and A are each as defined above, one of $R_a^1$ and $R_a^2$ is nitro while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_b^1$ and $R_b^2$ is hydroxyamino or amino while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_c^1$ and $R_c^2$ is amino while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_d^1$ and $R_d^2$ is protected amino while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_e^1$ and $R_e^2$ is protected hydroxy or protected hydroxy(lower)alkyl while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_f^1$ and $R_f^2$ is hydroxy or hydroxy(lower)alkyl while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_g^1$ and $R_g^2$ is protected carboxy while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, one of $R_h^1$ and $R_h^2$ is carboxy while the other is hydrogen, halogen, nitro, amino, protected amino, hydroxyamino, lower alkyl, hydroxy, protected hydroxy, sulfamoyl, carboxy, protected carboxy, mercapto, heterocyclic-carbonyl, heterocyclic-(lower)alkyl, lower alkylthio, hydroxy(lower)alkyl or protected hydroxy(lower)alkyl, $R^4$ is esterified carboxy, and X is a leaving group.

The compounds (II) and (IV) used in the Processes 1 and 4 are new and can be prepared, for example, by the following methods or a conventional manner.

Method A:

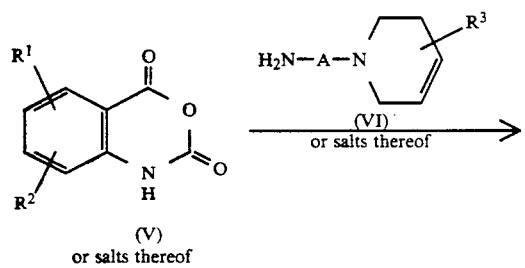

(V)
or salts thereof

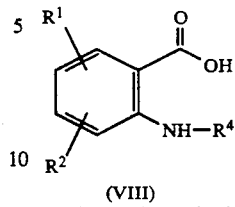

(VIII)
or its reactive derivative at the carboxy group, or salts thereof

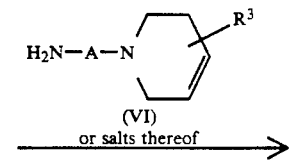

(VI)
or salts thereof

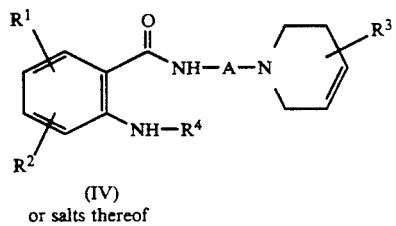

(IV)
or salts thereof

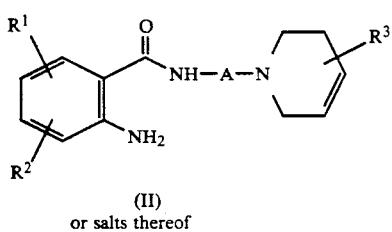

(II)
or salts thereof

Method B:

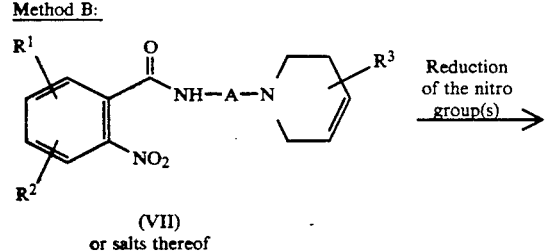

(VII)
or salts thereof

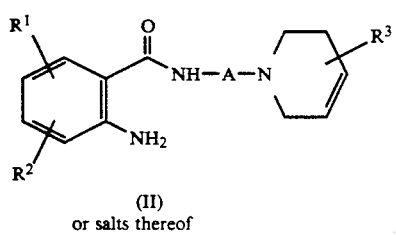

(II)
or salts thereof

Method C:

in which $R^1$, $R^2$, $R^3$, $R^4$ and A are each as defined above.

Some of the starting materials of the above Method A are new and can be prepared, for example, according to the method of Preparation as mentioned below, or in a conventional manner.

In the above and subsequent descriptions of the present specification, suitable examples and illustrations of the various definitions which the present invention includes within the scope thereof are explained in detail as follows.

The term "lower" is intended to mean 1 to 6 carbon atom(s), preferably 1 to 4 carbon atom(s), unless otherwise indicated.

Suitable "lower alkyl" may include straight or branched one such as methyl, ethyl, propyl, isopropyl, butyl, t-butyl, pentyl, hexyl, and the like.

Suitable "lower alkoxy" may include straight or branched one such as methoxy, ethoxy, propoxy, isopropoxy, butoxy, t-butoxy, pentyloxy, hexyloxy, and the like, in which the most preferable one may be methoxy.

Suitable "aryl which may have suitable substituent(s)" may include phenyl, tolyl, xylyl, cumenyl, mesithyl, naphthyl, and the like, each of which may be substituted by one or more, preferably one or two substituent(s) such as halogen (e.g. fluorine, chlorine, bromine, iodine), lower alkyl as mentioned above (e.g. methyl, etc.), and the like, in which more preferred example may be phenyl which is substituted or unsubstituted by a group consisting of halogen and lower alkyl, and the most preferred one may be phenyl, 4-chloro(or fluoro)phenyl and 4-tolyl.

Suitable "protected carboxy" may include carbamoyl, esterified carboxy wherein "esterified carboxy" can be referred to the ones as mentioned below, and the like.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester (e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxo-1,3-dioxol-4-yl)(lower)alkyl ester (e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester [e.g. mono- or di- or triphenyl(lower)alkyl ester, etc.] which may have at least one suitable substituent(s) (e.g. lower alkoxy, nitro, hydroxy, lower alkyl, etc.), for example, mono- or di- or triphenyl(lower)alkyl ester which may have (lower)alkoxy [e.g. benzyl ester, benzhydryl ester, trityl ester, phenethyl ester, 4-methoxybenzyl ester, 3,4-dimethoxybenzyl ester, bis(methoxyphenyl)methyl ester, etc.], nitrophenyl(lower)alkyl ester (e.g. 4-nitrobenzyl ester, etc.), [hydroxy]-(lower)alkylphenyl(lower)alkyl ester (e.g. 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be carbamoyl and lower alkoxycarbonyl.

Suitable "protected amino" may include amino protected by a conventional amino-protective group as mentioned below.

Suitable "amino-protective group" may include acyl such as aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, halogen as mentioned below, and the like, and preferable acyl having such substituent(s) may be nitroaralkoxycarbonyl (e.g. nitrobenzyloxycarbonyl, etc.), trihalo(lower)alkyl (e.g. trifluoroacetyl, etc.), and the like.

Preferable example of amino-protective group thus defined may be:
lower alkanoyl (e.g. acetyl, etc.);
trihalo(lower)alkanoyl such as trifluoro(lower)alkanoyl (e.g. trifluoroacetyl, etc.);
lower alkoxycarbonyl (e.g. ethoxycarbonyl, etc.);
carbamoyl;
N-(lower)alkylcarbamoyl (e.g. N-ethylcarbamoyl, etc.);
lower alkylsulfonyl (e.g. mesyl, ethylsulfonyl, etc.);
and the like.

"Protected hydroxy" means a hydroxy group protected by a conventional hydroxy-protective group, and suitable "hydroxy-protective group may include lower alkyl as defined above, acyl as defined above, ar(lower)alkyl such as mono-, di- or triphenyl(lower)alkyl (e.g. trityl, etc.), preferably lower alkyl and triphenyl(lower)alkyl, and the most preferably methyl and trityl.

Suitable heterocyclic group in "heterocyclic-carbonyl" and "heterocyclic-(lower)alkyl" may include 3 to 10, preferably 5 or 6-membered heteromonocyclic group containing at least one hetero atom such as oxygen atom, nitrogen atom and sulfur atom (e.g. morpholino, etc.), and the like.

Suitable lower alkyl group in "heterocyclic-(lower)alkyl" can be referred to the ones as mentioned above.

Suitable "halogen" may be fluorine, chlorine, bromine, iodine, and more preferred example may be chlorine.

Suitable "lower alkylene" may include straight or branched one such as methylene, ethylene, trimethylene, tetramethylene, pentamethylene, hexamethylene, methylmethylene, ethylethylene, propylene, and the like, in which the most preferred one may be tetramethylene.

Suitable "leaving group" may include imidazole, lower alkylimidazole (e.g. 2-methylimidazole, etc.), an acid residue such as halogen as mentioned above (e.g. chlorine, etc.), and the like.

Suitable "lower alkylthio" may include straight or branched one such as methylthio, ethylthio, propylthio, isopropylthio, butylthio, t-butylthio, pentylthio, hexylthio, and the like.

Suitable "esterified carboxy" means the same ones as mentioned in the explanation of protected carboxy, in which more preferable example may be lower alkoxycarbonyl and the most preferable one may be ethoxycarbonyl.

Suitable "hydroxy(lower)alkyl" may include hydroxymethyl, hydroxyethyl, hydroxypropyl, hydroxyhexyl, and the like.

Suitable "protected hydroxy(lower)alkyl" means hydroxy(lower)alkyl protected by a conventional hydroxy-protective group as mentioned in the explanation of "protected hydroxy", in which more preferable example may be lower alkoxy(lower)alkyl and triphenyl(lower)alkoxy(lower)alkyl, and the most preferable one may be methoxymethyl and trityloxymethyl.

The processes for the preparation of the object compound (I) of the present invention are explained in detail in the following.

(1) Process 1

The compound (I) or salts thereof can be prepared by reacting the compound (II) or salts thereof with the compound (III).

Suitable salts of the compound (II) may be acid addition salts such as those given for the compound (I).

Suitable example of the compound (III) may include N,N'-carbonyldiimidazole, N,N'-carbonylbis(2-methylimidazole), phosgene or its reactive equivalent (e.g. dimer or trimer thereof, etc.), and the like.

This reaction can be carried out in a conventional solvent which does not adversely influence the reaction such as dichloromethane, pyridine, N,N-dimethylformamide, 4-methyl-2-pentanone, tetrahydrofuran, etc., or a mixture thereof.

The reaction temperature is not critical and the reaction is usually carried out under from warming to heating.

(2) Process 2

The compound (I-b) or salts thereof can be prepared by subjecting the compound (I-a) or salts thereof to reduction of nitro group(s) of $R_a^1$ and/or $R_a^2$.

Suitable salts of the compounds (I-a) and (I-b) may be the same as those for the compound (I).

The present reaction is usually carried out by a conventional method as mentioned below.

REDUCTION METHOD

The reduction method applicable for this reaction may include conventional ones which are capable of converting a nitro group to a hydroxyamino group, for example, reduction using tin(II) chloride or zinc powder; reduction using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.); reduction using aluminum amalgam; electrolytic reduction; and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from warming to heating.

(3) PROCESS 3

The compound (I-d) or salts thereof can be prepared by introducing an amino-protective group(s) into the compound (I-c) or salts thereof.

Suitable salts of the compounds (I-c) and (I-d) may be the same as those for the compound (I).

Suitable introducing agent of the amino-protective group used in this reaction may be a conventional one which is capable of introducing the amino-protective group such as acyl as mentioned before, for example, lower alkyl isocyanate (e.g. ethyl isocyanate, etc.); alkali metal cyanate (e.g. potassium cyanate, etc.); lower alkyl halo(lower)alkanate (e.g. ethyl chloroformate, etc.); carboxylic acid, carbonic acid, sulfonic acid and their reactive derivative (e.g. an acid halide, an acid anhydride, an activated amide, an activated ester, etc.); and the like. Preferable example of such reactive derivative may include lower alkanoic acid halide (e.g. acetyl chloride, etc.); lower alkanesulfonyl halide (e.g. mesyl chloride, ethanesulfonyl chloride, etc.); a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid sulfonic acid (e.g. methanesulfonic acid, toluenesulfonic acid, etc.), mono(lower)alkyl ester of carbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride such as lower alkanoic anhydride (e.g. acetic anhydride, etc.), trihalo(lower)alkanoic anhydride (e.g. trifluoroacetic anhydride, etc.); an activated acid amide with a heterocyclic compound containing imino function such as imidazole, 4-substituted imidazole, dimethylpyrazole, triazole and tetrazole; an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.); and the like.

This reaction can be carried out in the presence of a base or an acid according to the introducing agent of the amino-protective group to be used.

Suitable base may include an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.).

In case that the introducing agent of the amino-protective group is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof, and further in case that the amino-introducing agent is in liquid, it can also be used as a solvent.

The reaction temperature is not critical and the reaction is usually carried out under from cooling to heating.

(4) PROCESS 4

The compound (I) or salts thereof can be prepared by reacting the compound (IV) or salts thereof with a base.

Suitable salts of the compound (IV) may be the same as those for the compound (I).

Suitable base used in this reaction may be the same as those given in the explanation of Process 3.

This reaction is usually carried out in a conventional solvent which does not adversely influence the reaction such as tetrahydrofuran, dioxane, water, methanol, ethanol, etc., or a mixture thereof.

The reaction temperature is not critical, and the reaction is usually carried out under from warming to heating.

(5) PROCESS 5

The compound (I-f) or salts thereof can be prepared by subjecting the compound (I-e) or salts thereof to a removal reacting of the hydroxy protective group(s) in $R_e^1$ and/or $R_e^2$.

Suitable salts of the compounds (I-e) and (I-f) may be the same as those for the compound (I).

The present reaction is usually carried out by a conventional method such as hydrolysis, reduction, and the like.

(i) HYDROLYSIS

The hydrolysis is preferably carried out in the presence of a base or an acid. Suitable base may include an alkalimetal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) REDUCTION

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

The removal reaction can be selected according to the kind of hydroxy protective group to be removed.

(6) PROCESS 6

The compound (I-h) or salts thereof can be prepared by subjecting the compound (I-g) or salts thereof to a removal reaction of the carboxy-protective group(s) in $R_g^1$ and/or $R_g^2$.

Suitable salts of the compounds (I-g) and (I-h) may be the same as those for the compound (I).

This reaction is usually carried out by a conventional method such as hydrolysis, reduction and the like.

The method of hydrolysis and reduction, and the reaction conditions (e.g. reaction temperature, solvent etc.) are substantially the same as those illustrated for removal reaction of the hydroxy-protective group of the compound (I-a) in Process 5, and therefore are to be referred to said explanation.

The object compound (I) obtained according to the Processes 1 to 6 can be isolated and purified in a conventional manner, for example, extraction, precipitation, fractional crystallization, recrystallization, chromatography, and the like.

Methods A to C for preparing the new starting compounds (II) and (IV) or salts thereof are explained in detail in the following.

(A) METHOD A

The compound (II) or salts thereof can be prepared by reacting the compound (V) or salts thereof with the compound (VI) or salts thereof.

Suitable salts of the compound (V) may be salts with bases such as those given for the compound (I).

Suitable salts of the compound (VI) may be the same acid addition salts as those for the compound (I).

This reaction is usually carried out in a conventional solvent which does not adversely influence the reaction such as dichloromethane, pyridine, N,N-dimethylformamide, 4-methyl-2-pentanone, tetrahydrofuran, etc., or a mixture thereof.

The reaction temperature is not critical and the reaction is usually carried out under from warming to heating.

(B) METHOD B

The compound (II) or salts thereof can be prepared by reducing the nitro group of the compound (VII) or salts thereof.

Suitable salts of the compound (VII) may be the same as those for the compound (I).

The method of reduction and the reaction conditions (e.g. reaction temperature, solvent, etc.) are substantially the same as those illustrated in Process 2, and therefore are to be referred to said explanation.

(C) METHOD C

The compound (IV) or salts thereof can be prepared by reacting the compound (VIII) or its reactive derivative at the carboxy group, or salts thereof with the compound (VI) or salts thereof.

Suitable salts of the compound (VIII) may be the same as those for the compound (I).

Suitable reactive derivative of the compound (VIII) may include an acid halide, an acid anhydride, an activated amide, an activated ester, and the like.

The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid etc.), dialkylphosphorous acid, lower alkanesulfonic acid (e.g. methanesulfonic acid, ethanesulfonic acid, etc.), sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl $[(CH_3)_2N^{30}=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-[1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (VIII) to be used.

When the compound (VIII) is used in free acid from or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketeneN-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as those given in the explanation of Process 3.

The reaction is usually carried out in a conventional solvent which does not adversely influence the reaction such as water, methanol, ethanol, acetone, dioxane, acetonitrile, chloroform, methylene chloride, ethylene chloride, tetrahydrofuran, ethyl acetate, N,N-dimethylformamide, pyridine, etc. or a mixture thereof.

The reaction temperature is not critical, and the reaction is usually carried out under warming to heating.

The object quinazoline derivatives (I) stimulate presynaptic(neuronal) and/or postsynaptic(vascular) dopamine receptors that mediate inhibition of neurogenic release of catecholamine and/or dilatation of renal vasculature and remission of parkinsonism, respectively. Quinazoline derivatives (I) effect on the cardiovascular system as a consequence of its interaction with dopaminergic and adrenergic receptors.

The object compound (I) and pharmaceutically acceptable salts thereof of the present invention are novel and display dopamine receptor stimulating effects;

5-HT receptor antagonism, especially 5-HT$_2$ receptor antagonism; $\alpha_1$ receptor antagonist; and the like, and are useful as a dopamine receptor agonist; 5-HT receptor antagonist, especially 5-HT$_2$ receptor antagonist; $\alpha_1$ receptor antagonist; and the like, for treating or preventing hypertension and other cardiovascular disorders (e.g. angina pectoris, congestive heart failure, myocardial infarction, etc.); Parkinsonism; hyperprolactinemia; disorders of peripheral perfusion such as Raynaud's phenomenon, Burger's diseases, and intermittent claudication; thrombotic and/or smooth muscle cell proliferative disease such as restenosis after percutaneous transluminal coronary angioplasty; hypercholesterolemia; urinary disturvance; and the like.

The compound (I) and pharmaceutically acceptable salts thereof may be also useful as a adrenolytic, tranquilizer, sedative, anti-emetic, hypothermic, skeletal muscle relaxant, anti-inflammatory, hypoglycemic, or anti-viral agent.

Now in order to show the utility of the object compound (I) and pharmaceutically acceptable salts, the test data on dopamine receptor stimulating effects of the representative compound of the compound (I) of this invention are shown in the following.

TEST COMPOUND

Compound A [The product of Example 2]
Compound B [The product of Example 12]

Test 1 [Dopamine receptor (DA$_2$ receptor) binding assay]

TEST METHOD 1

The affinity for DA$_2$ receptor of a Test Compound was determined following in vitro receptor binding assays.

Male rats weighing 150–300g were decapitated and the striatum were dissected from their brains. The tissue was homogenized in 30 volumes of buffer which consisted of 50 mM Tris-HCl (pH 7.4 at 25° C.), 120 mM sodium chloride, 5 mM potassium chloride, 1 mM calcium chloride, 1 mM magnesium chloride, 10 $\mu$M pargirine, and 0.1% ascorbic acid. The homogenate was centrifuged at 50,000 g for 15 minutes. The pellet was resuspended in 30 volumes of the buffer. The tissue suspension was centrifuged and suspended again in the same way.

Incubation tubes received 100 $\mu$l of [phenyl-4-$^3$H]spiperone, 100 $\mu$l of the Test Compound and 0.8 ml of tissue suspension during binding assays. The concentration of [phenyl-4-$^3$H]spiperone was 0.2 nM. The final tissue concentration of rat striatum was 160 $\mu$g/ml. The tubes were incubated at 37° C. for 10 minutes, and then filtered under vacuum through Whatman GF/B filters and washed three times with 3 ml of ice-cold buffer. The filters were counted by liquid scintillation counter.

Specific binding of the [$^3$H]spiperone was determined in the presence of 1 $\mu$M butaclamol. The IC$_{50}$ value of the Test Compound was calculated from the data of [$^3$H]spiperone binding in the presence of $10^{-9}$M, $10^{-8}$M, $10^{-7}$M and $10^{-6}$M Test Compound.

TEST RESULT 1

| Test Compound | IC$_{50}$ (M) |
| --- | --- |
| Compound A | $8.1 \times 10^{-9}$ |

Test 2 [Inhibition of reserpine-induced DOPA accumulation]

TEST METHOD 2

Male SD rats weighing 300–400 g were used in this test. Rats were pretreated with reserpine (1 mg/kg, S.C.) 17–19 hours before sacrifice and then fasted. Test Compound was given orally to the rats 2 hours before sacrifice. [m-Hydroxybenzylhydrazine (100 mg/kg, i.p.) was given 30 minutes before sacrifice.] Each rat was exposed to microwaves using a head-focus microwave applicator for 1.5 seconds. The whole brain was removed and further separated into the striatum.

DOPA was determined as follows; the striatum was homogenized in 9 volumes of 0.1N perchloric acid solution (0.4% EDTA.2Na). The homogenate was centrifuged at 10,000 rpm for 1 minutes. The supernatant was applied to high performance liquid chromatography.

TEST RESULT 2

| Test Compound | dose (mg/kg) | Inhibition (%) |
| --- | --- | --- |
| Compound A | 3.2 | 33 |

Test 3 [Hypotensive effect on spontaneous hypertensive rats]

TEST METHOD 3

15 to 25-Week-old male spontaneous hypertensive rats with mean arterial blood pressure of about 160–200 mmHg, weighing 300–350 g, were used. The animals were cannulated in the left femoral artery and the mean blood pressure and heart rate were measured with a pressure-transducer. The animals were deprived of food for about 18 hours before oral dosing. The Test Compound was suspended in 0.5% methylcellulose, and given orally.

TEST RESULT 3

The maximum decrease of blood pressure (%) is shown in Table.

| Test Compound | dose (mg/kg) | Maximum decrease of blood pressure (%) |
| --- | --- | --- |
| Compound A | 0.32 | 34 |

Test 4 : [Serotonin (5HT) antagonistic activity]

TEST METHOD 4

Male normotensive Wistar rats, weighing 250 to 300 g, were anesthetized by pentabarbital Na (50 mg/kg, i.p.) and the common carotid artery and external jugular vein were cannulated, respectively, for blood pressure measurement with a pressure-transducer and for drug administration.

The trachea was cannulated, and the rats were pithed by inserting a steel rod into the spiral canal via an eye orbit and immediately artifically respired. Atropine at 1 mg/kg and d-tubocurarine at 1 mg/kg was intraveneouly administered through the cannula. To evaluate the antagonistic effect of test compounds, pressor response to iv injection of 5HT (3.2, 10, 32 $\mu$g/kg) were obtained before and 10 min after i.v. doses of test compounds. Each pressor response curve to 5HT was plotted, and the antagonistic potency of test compound was expressed as the change of the 5HT ED$_{30}$ values (i.v.

doses of 5HT producing a 30 mmHg increase in diastolic blood pressure).

TEST RESULT

| Test compound | dose (g/kg) | ED$_{30}$ (μg/kg) | |
|---|---|---|---|
| | | pre | post |
| Compound A | 0.32 | 14 | 25 |
| Compound B | 0.32 | 8 | 32 |

Test 5 [α1-adrenoceptor binding assay]

TEST METHOD 5

Male Wistar rats (200–250 g) were killed by decapitation and the brain was placed in ice-cold buffer (0.25M sucrose, 5 mM Tris/HCl, 1 mM MgCl$_2$, pH 7.5). Whole brain was homogenized in 10–20 volume (w/v) of ice-cold buffer for 20 strokes using a motor-drived Teflon-glass homogenizer. The homogenate was centrifuged at 1,000 g for 10 min at 4° C., and the pellet was discarded. The supernatant was centrifuged at 30,000 g for 20 min at 4° C. The pellet obtained was washed by resuspension in 20 ml ice-cold 50 mM Tris/HCl, 10 mM MgCl$_2$ buffer (pH 7.5) and recentrifuged at 30,000 g for 20 min at 4° C. The final pellet was resuspended in 15 volumes of original wet weight of 50 mM Tris/HCl, 10 mM MgCl$_2$ buffer (pH 7.5) for use in the assays.

For $^3$H-Prazosin binding to rat brain, membrane suspensions prepared from rat whole brain (0.3–0.4 mg protein) were incubated by constant shaking for 20 min at 30° C. with $^3$H-Prazosin (0.6 μM) and increasing concentrations of test compounds ($10^{-6}$- $10^{-9}$M) in a total volume of 550 μl of 50 mM Tris/HCl, 10 mM MgCl$_2$ buffer containing 0.1 mg/ml bovine serum albumin (pH 7.5). The incubation, which was performed in duplicate, was terminated by adding 4 ml of ice-cold 50 mM Tris/HCl, 10 mM MgCl$_2$ buffer (pH 7.5) followed by rapid filtration through Whatman GF/C glass filter disks. The filter disks were washed 3 times with 4 ml ice-cold 50 mM Tris/HCl, 10 mM MgCl$_2$ buffer (pH 7.5), and dried for 2 hours at 80° C. These filter disks were counted by liquid scintillation counter with an efficacy of 40%. Nonspecific binding was defined as nondisplaceable binding in the presence of 10 μM phentolamine, while specific binding was defined as the difference between total and non specific binding. The concentration of the test compound inhibiting 50% of the specific binding of $^3$H-Prazosin was calbulated by log profit analysis of the binding data.

TEST RESULT 5

| Test Compound | IC$_{50}$ (M) |
|---|---|
| Compound A | $2.0 \times 10^{-8}$ |
| Compound B | $3.8 \times 10^{-8}$ |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between about 0.001 mg and about 300 mg, preferably about 0.1 mg to about 50 mg per day may be administered to a patient. An average single dose of about 0.001 mg, 0.01 mg, 0.03 mg, 0.1 mg, 0.3 mg, 0.6 mg, 1.0 mg, 3.0 mg, 10.0 mg, 50.0 mg, 100.0 mg, of the object compound (I) of the present invention may be used as adrenolytic, hypotensive, cardiovascular, tranquilizer, sedative, anti-emetic, hypothermic, skeletal muscle relaxant, anti-inflammatory, and anti-viral agents.

The following Preparations and Examples are given for the purpose of illustrating this invention in more detail.

PREPARATION 1

1) A mixture of 4-(4-chlorophenyl)-1,2,3,6-tetrahydropyridine hydrochloride (11.5 g), 4-chlorobutyronitrile (5.7 g), sodium iodide (7.5 g), potassium carbonate (13.8 g) and 2-butanone (100 ml) was stirred under reflux for 8 hours. After filtration and evaporation of the filtrate, the crude residue was dissolved in ethyl acetate, washed with brine, dried over magnesium sulfate and evaporated to give an oil (15.6 g). The oil was chromatographed on silica gel (450 g) to afford crystals of 4-[4-[4-(4-chlorophenyl)-1,2,3,6-tetrahydropyridin-1-yl]butyronitrile (13.0g).

mp : 71°–73° C.

IR (Nujol) : 2900, 1490, 1400 cm$^{-1}$

NMR (CDCl$_3$, δ) : 1.84–1.97 (2H, m), 2.43–2.65 (6H, m), 2.70 (2H, t, J=5Hz), 3.17 (2H, t, J=5Hz), 6.02–6.09 (1H, m), 7.27–7.34 (4H, m)

2) To a stirred solution of 4-[4-(4-chlorophenyl)-1,2,3,6-tetrahydropyridin-1-yl]butyronitrile (13.0 g) in dry tetrahydrofuran (130 ml) was added 1M solution of lithium aluminum hydride in tetrahydrofuran (60 ml), and the mixture was stirred for 1 hour. After saturated aqueous ammonium chloride solution (10 ml) was added with stirring, the organic layer was separated by decantation, dried over magnesium sulfate and evaporated to dryness to give an oil of 4-[4-[4-(4-chlorophenyl)-1,2,3,6-tetrahydropyridin-1-yl]butylamine (7.18 g).

IR (Neat) : 3250, 2930, 1660 cm$^{-1}$

NMR (CDCl$_3$, δ) : 1.47–1.68 (4H, m), 2.14 (2H, br s), 2.42–2.78 (6H, m), 3.14 (2H, t, J=5Hz), 3.78 (2H, t, J=5Hz), 6.03–6.09 (1H, m), 7.23–7.37 (4H, m)

PREPARATION 2-1)

A mixture of 4-nitroisatonic anhydride (0.62 g), 4-(4-phenyl-1,2,3,6-tetrahydropyridin-1-yl)butylamine (0.83 g) and chloroform (10 ml) was stirred under reflux for 1 hour. After evaporation of the solvent, the crude residue was chromatographed on silica gel to give crystals of 2-amino-4-nitro-N-[4-(4-phenyl-1,2,3,6-tetrahydropyridin-1-yl)butyl]benzamide (0.56 g).

mp : 135°–137° C.

IR (Nujol) : 3450, 3300, 1630 cm$^{-1}$

NMR (CDCl₃, δ) : 1.72–1.82 (4H, m), 2.50–2.60 (4H, m), 2.73 (2H, t, J=5Hz), 3.17 (2H, t, J=5Hz), 3.47 (2H, d, J=5Hz), 6.75 (2H, s), 6.00–6.07 (1H, m), 7.16–7.43 (8H, m), 8.12 (1H, br s)

PREPARATION 2-2)

2-Amino-N-[4-{4-(4-chlorophenyl)-1,2,3,6-tetrahydropyridin-1-yl}butyl]benzamide was obtained in 94.7% yield in substantially the same manner as that of Preparation 2-1).

mp 140°–142° C.

IR (Nujol) : 3320, 3260, 1605 cm⁻¹

NMR (CDCl₃, δ) : 1.77 (4H, t, J=5Hz), 2.50–2.62 (4H, m), 2.72 (2H, t, J=5Hz), 3.12–3.18 (2H, m), 3.45 (2H, d, J=5Hz), 5.52 (2H, br s), 6.02–6.07 (1H, m), 6.51 (1H, t, J=8Hz), 6.65 (1H, d, J=5Hz), 6.95 (1H, br s), 7.14 (1H, t, J=8Hz), 7.25–7.31 (5H, m)

The following compounds were obtained in substantially the same manner as that of Preparation 2-1).

PREPARATION 3

2-Amino-5-chloro-N-[4-(4-phenyl-1,2,3,6-tetrahydropyridin-1-yl)butyl]benzamide

IR (Nujol) : 3400 (br), 1620, 1570 cm⁻¹

PREPARATION 4

2-Amino-4-chloro-N-[4-(4-phenyl-1,2,3,6-tetrahydropyridin-1-yl)butyl]benzamide

NMR (CDCl₃, δ) : 1.65–1.80 (4H, m), 2.45–2.60 (4H, m), 2.70 (2H, t, J=5Hz), 3.15 (2H, dd, J=6Hz, 3Hz), 3.45 (2H, dd, J=12Hz, 6Hz), 5.60 (1H, br s), 6.05–6.10 (1H, m), 6.40 (1H, dd, J=8Hz, 1.5Hz), 6.60 (1H, d, J=1.5Hz), 7.20 (1H, d, J=8Hz), 7.25–7.40 (7H, m)

PREPARATION 5-1)

A solution N-(4-bromobutyl)phthallmide (0.85 g), 4-(4-methylphenyl)-1,2,3,6-tetrahydropyridine hydrochloride (0.63 g) and triethylamine (0.91 g) in dry acetonitrile (10 ml) was refluxed for 3 hours. After evaporation of the solvent, crude residue was dissolved in ethyl acetate, washed with water, sat. ammonium chloride solution and brine successively, dried over magnesium sulfate and evaporated to give a yellow solid of N-[4-{4-(4-methylphenyl)-1,2,3,6-tetrahydropyridin-1-yl}-butyl]phthalimide (0.99 g).

NMR (CDCl₃, δ) : 1.60–1.85 (4H, m), 2.35 (3H, s), 2.50–2 60 (4H, m), 2.70 (2H, t, J=5Hz), 3.10–3.20 (2H, m), 3.25 (2H, t, J=7Hz), 5.95–6.05 (1H, m), 7.10 (2H, d, J=8Hz), 7.25 (2H, d, J=8Hz), 7.70–7.85 (4H, m)

PREPARATION 5-2)

A solution of N-[4-{4-(4-methylphenyl)-1,2,3,6-tetrahydropyridin-1-yl}butyl]phthalimide (0.98 g), hydrazine hydrate [0.17 g) in methanol (10 ml) was stirred under reflux for 4 hours. After evaporation of the solvent, the crude residue was mixed with chloroform and 1N sodium hydroxide. The chloroform layer was separated, dried over magnesium sulfate and evaporated to give an oil of 4-[4-(4-methylphenyl)-1,2,3,6-tetrahydropyridin-1-yl]butylamine (0.96 g).

NMR (CDCl₃, δ) : 1.55–1.70 (4H, m), 2.30 (3H, s), 2.45–2.60 (4H, m), 2.70 (2H, t, J=5Hz), 3.60–3 70 (4H, m), 5.95–6.05 (1H, m), 7.10 (2H, d, J=8Hz), 7.25 (2H, d, J=8Hz)

The following compounds were obtained in substantially the same manner as that of Preparation 2-1).

PREPARATION 5-3)

2-Amino-N-[4-{4-(4-methylphenyl)-1,2,3,6-tetrahydropyridin-1-yl}butyl]benzamide

NMR (CDCl₃, δ) : 1.65–1.75 (4H, m), 2.35 (3H, s), 2.45–2.60 (4H, m), 2.70 (2H, t, J=5Hz), 3.10–3.15 (2H, m), 5.5 (2H, br s), 5.95–6.05 (1H, m), 6.50 (1H, td, J=8Hz, 1.5Hz), 6.65 (1H, dd, J=8Hz, 1.5Hz), 7.00 (1H, br s), 7.05–7.30 (6H, m)

PREPARATION 6

2-Amino-N-[4-{4-(4-fluorophenyl)-1,2,3,6-tetrahydropyridin-1-yl}butyl]benzamide

NMR (CDCl₃, δ) : 1.65–1.75 (4H, m), 2.45–2.60 (4H, m), 2.70 (2H, t, J=5Hz), 3.15 (2H, dd, J=6Hz, 2.5Hz), 3.40–3.50 (2H, m), 5.45–5.55 (2H, br s), 5.55–5.65 (1H, m), 6.50 (1H, td, J=8Hz, 1.5Hz), 6.65 (1H, dd, J=7Hz, 1Hz), 6.40–7.05 (3H, m), 7.15 (1H, td, J=8Hz, 1.5Hz), 7.25–7.40 (2H, m)

PREPARATION 7-1)

To a solution of 2-amino-4-sulfamoylbenzoic acid (1.32 g) in 2N sodium hydroxide (6 ml) was added dropwise ethyl chloroformate (1.9 ml) and 2N sodium hydroxide on an ice bath. After stirring for 3 hours, the reaction mixture was acidified with 1N hydrochloric acid, extracted with ethyl acetate. Combined organic extracts were washed in turn with water and brine, dried over magnesium sulfate and evaporated to give an amorphous of 2-ethoxycarbonylamino-4-sulfamoylbenzoic acid (1.99 g).

NMR (CDCl₃, δ) : 1.33 (3H, t, J=7Hz), 2.80 (2H, br s), 4.20 (2H, q, J=7Hz), 7.70 (1H, dd, J=8Hz, 2Hz), 8.20 (2H, m), 9.00 (1H, d, J=2Hz)

PREPARATION 7-2)

2-Ethoxycarbonylamino-4-sulfamoyl-N-[4-(4-phenyl-1,2,3,6-tetrahydropyridin-1-yl)butyl]benzamide was obtained in substantially the same manner as that of Preparation 9-1).

NMR (CDCl₃, δ) : 1.25 (3H, t, J=6Hz), 1.70–2.30 (4H, m), 2.80–3.00 (2H, m), 3.10–3.60 (6H, m), 4.10 (2H, d, J=6Hz), 6.00–6.10 (1H, m), 7.30–7.40 (5H, m), 7.50 (1H, d, J=7H), 8.10–8.20 (1H, m), 8.60 (1H, d, J=1.5Hz)

PREPARATION 8

2-Amino-5-nitro-N-[4-(4-phenyl-1,2,3,6-tetrahydropyridin-1-yl)butyl]benzamide was obtained in substantially the same manner as that of Preparation 2-1).

NMR (CDCl₃, δ) : 1.70–1.85 (4H, m), 2.35–2.45 (2H, m), 2.55 (2H, t, J=6Hz), 2.70 (2H, t, J=6Hz), 3.25 (2H, dd, J=6Hz, 2.5Hz), 3.45 (2H, dd, J=12Hz, 6Hz), 5.95–6.00 (1H, m), 6.35–6.45 (2H, br s), 6.45 (1H, d, J=9Hz), 7.15–7.35 (5H, m), 7.85 (1H, dd, J=9Hz, 2.5Hz), 8.10–8.20 (1H, m), 8.25 (1H, d, J=2.5Hz)

PREPARATION 9-1)

To a solution of 4-methoxy-2-nitrobenzoic aid (1.3 g) in dry tetrahydrofuran (15 ml) was added thionyl chloride (2.86 ml) and the mixture was refluxed for 1.5 hours. After evaporation of the solvent and excess thionyl chloride, the residue was dissolved in dry methylene chloride (10 ml), which was added to a solution of 4-(4-phenyl-1,2,3,6-tetrahydropyridin-1-yl)butylamine hydrochloride (0.87 g) and triethylamine (2.0 g) in dry methylene chloride (20 ml) on an ice-bath. After stirring for 1.5 hours, the reaction mixture was washed with water, sat. sodium bicarbonate solution and brine successively, dried over magnesium sulfate and evaporated. The crude residue was chromatographed on silica gel (20 g, chloroform and methanol (50:1-9:1, V/V) as an eluent] to give an oil of 4-methoxy-2-nitro-N-[4-(4-phenyl1,2,3,6-tetrahydropyridin-1-yl)butyl]benzamide (1.2 g).

NMR (CDCl$_3$, δ) : 1.70–1.85 (4H m) 2.20–2.35 (2H, m), 2.45–2.55 (2H, m), 2.60 (2H, t, J=6Hz), 3.00 (2H, dd, J=6Hz, 3Hz), 3.40–3.50 (2H, m), 3.60 (3H, s), 5.75–5.85 (1H, m), 6.80 (1H, dd, J=9Hz, 2Hz), 7.15–7.35 (7H, m), 8.80 (1H, br s)

PREPARATION 9-2)

A mixture of 4-methoxy-2-nitro-N-[4-(4-phenyl-1,2,3,6-tetrahydropyridin-1-yl)butyl]benzamide (1 g), tin(II) chloride (1.39 g) and ethanol (20 ml) was stirred under reflux for 0.5 hour. After cooling, sat. sodium bicarbonate solution was added and the mixture was diluted with chloroform (50 ml). A chloroform layer was separated, washed in turn with water and brine, dried over magnesium sulfate and evaporated. Crude residue (0.93 g) was chromatographed on a silica gel [13 g, chloroform and methanol (50:1-20:1, V/V) as an eluent] to give 2-Amino-4-methoxy-N-[4-(4-phenyl-1,2,3,6-tetrahydropyridin-1-yl)butyl]benzamide (0.54 g).

NMR (CDCl$_3$, δ) : 1.65–1.75 (4H, m), 2.50–2.65 (4H, m), 2.70 (2H, t, J=5Hz), 3.15 (2H, dd, J=6Hz, 2Hz), 3.35–3.45 (2H, m), 3.70 (3H, s), 5.70 (1H, br s), 6.00–6.10 (2H, m), 6.90 (1H, br s), 7.20–7.40 (7H, m)

PREPARATION 10

2-Amino-N-[4-[4-phenyl-1,2,3,6-tetrahydropyridin-1-yl)butyl]benzamide was obtained in substantially the same manner as that of Preparation 2-1).

NMR {CDCl$_3$, δ) : 1.65–1.80 (4H, m), 2.55–2.65 (4H, m), 2.80 (2H, t, J=5Hz), 3.25 (2H, dd, J=5Hz, 2.5Hz), 3.45 (2H, dd, J=12Hz, 6Hz), 5.50 (1H, br s), 6.00–6.10 (1H, m), 6.55 (1H, td, J=7.5Hz, 1Hz), 6.65 (1H, dd, J=8Hz, 1.5Hz), 7.10 (2H, br s), 7.15 (1H, td, J=8Hz, 1.5Hz), 7.15–7.40 (6H, m)

PREPARATION 11-1)

A mixture of 4-methoxycarbonyl-3-nitrobenzoic acid (2.25 g), 1M borane in tetrahydrofuran solution (50 ml) and dry tetrahydrofuran (45 ml) was stirred at room temperature for 48 hours. To this mixture, methanol (2 ml) and 1N hydrochloric acid (10 ml) were added and then the solvents were evaporated off. The crude residue was taken up with ethyl acetate, washed in turn with water and sat. sodium bicarbonate solution, dried over magnesium sulfate and evaporated to give an oil which was chromatographed on silica gel. Elution with toluene-chloroform (1:1) gave methyl 4-hydroxymethyl-2-nitrobenzoate (1.85 g).

NMR (CDCl$_3$, δ) : 3.95 (3H, s), 4.82 (2H, s), 7.63 (1H, dd, J=8H, 2Hz), 7.70 (1H, d, J=8Hz), 7.88 (1H, d, J=2Hz)

PREPARATION 11-2)

A mixture of methyl 4-hydroxymethyl-2-nitrobenzoate (1.49 g), thionyl chloride (1.08 g), dry pyridine (0.1 g), dry ether (70 ml) and dry tetrahydrofuran (20 ml) was stirred overnight. The reaction mixture was washed in turn with 1N hydrochloric acid and sat. sodium bicarbonate solution, dried over magnesium sulfate and evaporated to give methyl 4-chloromethyl-2-nitrobenzoate (1.60 g).

NMR (CDCl$_3$, δ) : 3.93 (3H, s), 4.65 (2H, s), 7.70 (1H, dd, J=8Hz, 2Hz), 7.77 (1H, d, J=8Hz), 7.95 (1H, d, J=2Hz)

PREPARATION 11-3)

A mixture of methyl 4-chloromethyl-2-nitrobenzoate (1.6 g), 28% sodium methoxide-methanol solution (2.5 ml) in methanol [16 ml] was stirred under reflux for 24 hours. To this mixture, water (5 ml) was added and the mixture was stirred for 2 hours, acidified with 1N hydrochloric acid, extracted with ethyl acetate. The combined organic extract was washed with water, dried over magnesium sulfate and evaporated to give 4-methoxymethyl-2-nitrobenzoic acid (0.84 g).

NMR (CDCl$_3$, δ) : 3.48 (3H, s), 4.60 (2H, s), 7.63 (1H, dd, J=8Hz, 2Hz), 7.80 (1H, d, J=2Hz), 7.90 (1H, d, J=8Hz)

PREPARATION 11-4)

2-Nitro-4-methoxymethyl-N-[4-(4-methyl-1,2,3,6-tetrahydropyridin-1-yl)butyl]benzamide was obtained in substantially the same manner as that of Preparation 9-1).

NMR (CDCl$_3$, δ) : 1.75 (4H, m), 2.25 (2H, m), 2.50 (2H, m), 2.65 (2H, m), 3.02 (2H, m), 3.32 (3H, s), 3.47 (2H, m), 4.22 (2H, s), 5.73 (1H, m), 7.1–7.4 (7H, m), 7.68 (1H, s), 8.90 (1H, m)

PREPARATION 11-5)

2-Amino-4-methoxymethyl-N-[4-(4-phenyl-1,2,3,6-tetrahydropyridin-1-yl)butyl]benzamide was obtained in substantially the same manner as that of Preparation 9-2).

NMR (CDCl$_3$, δ) : 1.70 (2H, m), 1.95 (2H, m), 2.55 (4H, m), 2.72 (2H, m), 3.15 (2H, m), 3.32 (3H, s), 3.45 (2H, m), 4.30 (2H, s), 6.03 (1H, m), 6.45 (1H, dd, J=8Hz, 2Hz), 6.60 (1H, d, J=2Hz), 7.00 (1H, m), 7.2–7.4 (6H, m)

PREPARATION 12-1)

4-Carbamoyl-2-nitro-N-[4-(4-phenyl-1,2,3,6-tetrahydropyridin-1-yl)butyl]benzamide was obtained in substantially the same manner as that of Preparation 9-1).

NMR (DMSO-d$_6$, δ) :1.70 (4H, m), 1.85 (2H, m), 2.60 (2H, m), 2.75 (2H, m), 3.25 (2H, m), 3.40 (2H, m), 6.30 (1H, m), 7.35–7.60 (4H, m), 7.83 (1H, d, J=8Hz), 7.95 (1H, m), 8.35 (1H, dd, J=8Hz, 2Hz), 8.50 (1H, m), 8.60 (1H, m), 8.95 (1H, m)

PREPARATION 12-2)

2-Amino-4-carbamoyl-N-[4-(4-phenyl-1,2,3,6-tetrahydropyridin-1-yl)butyl]benzamide was obtained in substantially the same manner as that of Preparation 9-2).

NMR [DMSO-d$_6$, δ) : 1.55 (4H, m), 2.35–2.7 (6H, m), 3.05 (2H, m), 3.25 (2H, m), 6.15 (1H, m), 6.50 (2H, m), 7.00 (1H, d, J=8Hz), 7.2–7.6 (8H, m), 7.90 (1H, br s), 8.37 (1H, m)

PREPARATION 13-1)

4-Morpholinocarbonyl-2-nitro-N-[4-(4-phenyl-1,2,3,6-tetrahydropyridin-1-yl)butyl]benzamide was obtained in substantially the same manner as that of Preparation 9-1).

IR (Nujol) : 1660, 1640 cm$^{-1}$

PREPARATION 13-2)

2-Amino-4-morpholinocarbonyl-N-[4-(4-phenyl-1,2,3,6-tetrahydropyridin-1-yl)butyl]benzanide was obtained in substantially the same manner as that of Preparation 9-2).

NMR (DMSO-d$_6$, δ) : 1.55 (4H, m), 2.35–2.65 (6H, m), 3.05 (2H, m), 3.25 (2H, m), 3.60 (8H, m), 6.15 (1H, m), 6.50 (3H, m), 6.70 (1H, d, J=2Hz), 7.2–7.6 (6H, m), 8.34 (1H, t, J=6Hz)

PREPARATION 14-1)

Methyl 4-morpholinomethyl-2-nitrobenzoate was obtained in substantially the same manner as that of the former part of Preparation 11-3).

NMR (CDCl$_3$, δ) : 2.50 (4H, m), 3.61 (2H, s), 3.75 (4H, m), 3.93 (3H, s), 7.6–8.0 (3H, m)

PREPARATION 14-2)

4-Morpholinomethyl-2-nitrobenzoic acid was obtained in substantially the same manner as that of the latter part of Preparation 11-3).

NMR (CDCl$_3$, δ) : 2.40 (2H, m), 2.51 (2H, m), 3.60 (4H, m), 7.7–7.9 (3H, m)

PREPARATION 14-3)

4-Morpholinomethyl-2-nitro-N-[4-(4-phenyl-1,2,3,6-tetrahydropyridin-1-yl)butyl]benzamide was obtained in substantially the same manner as that of Preparation 11-4).

NMR (CDCl$_3$, δ) : 1.83 (4H, m), 2.37 (4H, m), 2.95 (2H, m), 2.71 (2H, m), 2.87 (2H, m), 3.25 (2H, m), 3.33 (2H, s), 3.50 (2H, m), 3.68 (4H, m), 5.82 (1H, m), 7.2–7.4 (7H, m), 7.82 (1H, s), 8.49 (1H, m)

PREPARATION 14-4)

2-Amino-4-morpholinomethyl-N-[4-(4-phenyl-1,2,3,6-tetrahydropyridin-1-yl)butyl]benzamide was obtained in substantially the same manner as that of Preparation 11-5).

NMR (CDCl$_3$, δ) : 1.75 (4H, m), 2.40 (4H, m), 2.65 (4H, m), 2.85 (2H, m), 3.30 (2H, m), 3.33 (2H, s), 3.45 (2H, m), 3.70 (4H, m), 5.55 (2H, br s), 6.02 (1H, m), 6.50 (1H, dd, J=8Hz, 1Hz), 6.64 (1H, s), 7.04 (1H, m), 7.2–7.4 (6H, m)

PREPARATION 15

2-Amino-5-methoxycarbonyl-N-[4-(4-phenyl-1,2,3,6-tetrahydropyridin-1-yl)butyl]benzamide was obtained in substantially the same manner as that of Preparation 2-1).

IR (CHCl$_3$) : 3500, 3350, 2940, 1700, 1640, 1615 cm$^{-1}$

PREPARATION 16-1)

A mixture of methyl 4-hydroxymethyl-2-nitrobenzoate (1.06 g) trityl chloride (1.67 g) in dry pyridine (20 ml) was stirred at 80° C. for 8 hours. The reaction mixture was diluted with water, acidified with 6N hydrochloric acid, and extracted with ethyl acetate. The combined organic extract was washed with 1N hydrochloric acid, saturated sodium bicarbonate solution and brine successively, dried over magnesium sulfate and evaporated to give an oil, which was crystallized from methanol to afford methyl 2-nitro-4-trityloxymethylbenzoate (1.87 g)

NMR (CDCl$_3$, δ): 3.41 (3H, s), 4.32 (2H, s), 7.32 (9H, m), 7.50 (6H, m), 7.64 (1H, dd, J=8, 1.5Hz), 7.72 (1H, d, J=8Hz), 7.85 (1H, d, J=1.5Hz)

PREPARATION 16-2)

2-Nitro-4-trityloxymethylbenzoic acid was obtained in substantially the same manner as that of Preparation 11-3).

NMR (CDCl$_3$, δ): 4.23 (2H, s), 7.25 (9H, m), 7.43 (6H, m), 7.52 (1H, m), 7.75 (2H, m)

PREPARATION 16-3)

2-Nitro-N-[4-(4-phenyl-1,2,3,6-tetrahydropyridin-1-yl)butyl]-4-trityloxymethylbenzamide was obtained in substantially the same manner as that of Preparation 11-4).

NMR (CDCl$_3$, δ): 1.80 (4H, m), 2.25 (2H, m), 2.55 (2H, m), 2.68 (2H, m), 3.06 (2H, m), 3.49 (2H, m), 4.00 (2H, s), 5.76 (1H, m), 7.07 (5H, m), 7.25–7.50 (17H, m), 7.70 (1H, s), 8.83 (1H, m)

PREPARATION 16-4)

2-Amino-N-[4-(4-phenyl-1,2,3,6-tetrahydropyridin-1-yl)butyl]-4-trityloxymethylbenzamide was obtained in substantially the same manner as that of Preparation 11-5).

NMR (CDCl$_3$, δ):1.71 (4H, m), 2.57 (4H, m), 2.75 (2H, m), 3.19 (2H, m), 3.45 (2H, m), 4.01 (2H, s), 5.60 (2H, brs), 6.05 (1H, m), 6.50 (1H, dd, J=8, 1.5Hz), 6.73 (1H, d, J=1.5Hz), 6.97 (1H, m), 7.15–7.40 (14H, m), 7.47 (6H, m)

EXAMPLE 1-1)

A mixture of 2-amino-4-nitro-N-[4-(4-phenyl-1,2,3,6-tetrahydropyridin-1-yl)butyl]benzamide (0.52 g) and carbonyldiimidazole (0.43 g) in dry tetrahydrofuran (10 ml) was stirred under reflux for 2 hours. After evaporation of the solvent, the crude residue was crystallized and recrystallized from ethanol to give crystals of 7-nitro-3-[4-(4-phenyl-1,2,3,6-tetrahydropyridin-1-yl)butyl]-1,2,3,4-tetrahydroquinazoline-2,4-dione (0.32 g).

mp 170°–171° C.

IR (Nujol) : 3270, 1720, 1640 cm$^{-1}$

NMR (DMSO-d$_6$, δ): 1.42–1.72 (4H, m), 2.38–2.49 (4H, m), 2.61 (2H, t, J=5Hz), 3.07 (2H, d, J=5Hz), 3.97 (2H, t, J=5Hz), 6.11–6.17 (1H, m), 7.19–7.43 (5H, m), 7.91–7.95 (2H, m), 8.15 (1H, d, J=8Hz)

EXAMPLE 1-2)

3-[4-{4-(4-Chlorophenyl)-1,2,3,6-tetrahydropyridin-1-yl}butyl]-1,2,3,4-tetrahydroquinazoline-2,4-dione was obtained in 42.1% yield in substantially the same manner as that of Example 1-1).

mp : 220° C. (dec.)

IR (Nujol) : 3100, 1705, 1650 cm$^{-1}$

NMR (DMSO-d$_6$, δ) : 1.56–1.82 (4H, m), 2.43–2.75 (6H, m), 3.10–3.20 (2H, m), 4.02 (2H, t, J=5Hz), 6.27–6.33 (1H, m), 7.32 (1H, t, J=8Hz), 7.45–7.59 (5H, m), 7.75 (1H, t, J=8Hz), 8.03 (1H, d, J=8Hz)

EXAMPLE 2

To a stirred solution of 7-nitro-3-[4-(4-phenyl-1,2,3,6-tetrahydropyridin-1-yl)butyl]-1,2,3,4-tetrahydroquinazoline-2,4-dione (0.2 g) in ethanol (10 ml) was added. Stannous chloride (0.46 g) and the mixture was refluxed for 30 minutes. After cooling, an aqueous sodium bicarbonate was added to adjust the pH to 7 and inorganic salts were filtered off through filter cell. The filter cake was washed with hot ethanol. Combined filtrate and washings were evaporated and the crude residue was washed in turn with water and cold ethanol, and then dried to give crystals of 7-hydroxyamino-3-[4-(4-phenyl-1,2,3,6-tetrahydropyridin-1-yl)butyl]-1,2,3,4-tetrahydroquinazoline-2,4-dione (85 mg).

mp : 187°–189° C.

IR (Nujol) : 3250, 1700 cm$^{-1}$

NMR (DMSO-d$_6$, δ) : 1.42–1.68 (4H, m), 2.38–2.52 (4H, m), 2.60 (2H, t, J=5Hz), 3.05 (2H, d, J=5Hz), 3.88 (2H, t, J=5Hz), 6.10–6.15 (1H, m), 6.51 (1H, d, J=8Hz), 6.54 (1H, s), 7.30–7.45 (6H, m), 7.65 (1H, d, J=8Hz), 8.75 (1H, s), 9.15 (1H, s)

EXAMPLE 3

A mixture of 7-nitro-3-[4-(4-phenyl-1,2,3,6-tetrahydropyridin-1-yl)butyl-1,2,3,4-tetrahydroquinazoline-2,4-dione (0.34 g), tin[II] chloride (0.76 g) in ethanol (16 ml) was stirred under reflux for 1 hour. After cooling, 1N sodium hydroxide was added and the solution was stirred. The organic layer was separated, dried over magnesium sulfate and evaporated to give a solid (0.33 g), which was recrystallized from ethyl acetate-hexane to give 7-amino-3-[4-(4-phenyl-1,2,3,6-tetrahydropyridin-1-yl)butyl]-1,2,3,4-tetrahydroquinazoline-2,4-dione (0.18 g).

mp : 250° C. [dec.]

IR (Nujol) : 3400, 3300, 3200, 1610, 1580, 1520 cm$^{-1}$

NMR (DMSO-d$_6$, δ) : 1.45–1.65 (2H, m), 1.70–1.90 (2H, m), 2.80 (2H, t, J=5Hz), 3.20 (4H, t, J=5Hz), 3.40 (2H, t, J=5Hz), 3.85 (2H, d, J=5Hz), 5.80 (1H, s), 6.20 (1H, s), 7.25–7.50 (8H, m)

EXAMPLE 4

7-Acetamido-3-[4-(4-phenyl-1,2,3,6-tetrahydropyridin-1-yl)butyl]-1,2,3,4-tetrahydroquinazoline-2,4-dione was obtained in substantially the same manner as that of Example 12 by using acetyl chloride instead of methanesulfonyl chloride.

mp : 250°–251° C.

IR (Nujol) : 3450, 1710, 1630, 1605 cm$^{-1}$

NMR (DMSO-d$_6$, δ) : 1.45–1.72 (4H, m), 2.42–2.68 (6H, m), 3.10 (2H, d, J=5Hz), 3.43 (3H, s), 3.94 (2H, t, J=5Hz), 6.18 (1H, s), 7.22–7.50 (6H, m), 7.73 (1H, s), 7.88 (1H, d, J=10Hz)

EXAMPLE 5

3-[4-[4-Phenyl-1,2,3,6-tetrahydropyridin-1-yl)butyl]-7-trifluoroacetamido-1,2,3,4-tetrahydroquinazoline-2,4-dione was obtained in substantially the same manner as that of Example 12 by using trifluoroacetic anhydride instead.

mp: 263°–265° C. (dec.)

IR (Nujol) : 3200, 1710, 1650, 1620, 1560 cm$^{-1}$

NMR (DMSO-d$_6$, δ) : 1.45–1.75 (4H, m), 2.67 (2H, t, J=5Hz), 3.10 (2H, t, J=5Hz), 3.45–3.95 (6H, m), 6.07 (1H, s), 7.20–7.40 (6H, m), 7.65 (1H, s), 7.85 (1H, s)

EXAMPLE 6

7-Ethoxycarbonylamino-3-[4-(4-phenyl-1,2,3,6-tetrahydropyridin-1-yl)butyl]-1,2,3,4-tetrahydroquinazoline-2,4-dione was obtained in substantially the same manner as that of Example 12 by using ethyl chloroformate instead.

mp : 200°–202° C. (dec.)

IR (Nujol) : 3270, 1700, 1640, 1550 cm$^{-1}$

NMR (DMSO-d$_6$, δ) : 1.05 (3H, t, J=8Hz), 1.20–1.47 (4H, m), 2.20 (4H, t, J=5Hz), 2.40 (2H, t, J=5Hz), 2.85 (2H, d, J=5Hz), 3.68 (2H, t, J=5Hz), 3.97 (2H, q, J=8Hz), 5.93 (1H, s), 6.90–7.25 (6H, m), 7.35 (1H, s), 7.60 (1H, d, J=8Hz)

EXAMPLE 7

A mixture of 7-amino-3-[4-(4-phenyl-1,2,3,6-tetrahydropyridin-1-yl)butyl]-1,2,3,4-tetrahydroquinazoline-2,4-dione (0.39 g), ethyl isocyanate (0.21 g) in dry tetrahydrofuran (40 ml) was stirred under reflux for 24 hours. After evaporation of the solvent, the crude residue was chromatographed on silica gel [chloroform and methanol (50:1) as eluent] to give crystals (0.17 g). Recrystallization of the crystals from isopropyl alcohol afforded 7-(3-ethylureido)-3-[4-(4-phenyl-1,2,3,6-tetrahydropyridin-1-yl)butyl]-1,2,3,4-tetrahydroquinazoline-2,4-dione (0.09 g).

mp : 220° C.

IR (Nujol) : 3330, 1700, 1640, 1540 cm$^{-1}$

NMR (DMSO-d$_6$, δ) : 1.02 (3H, t, J=8Hz), 1.42–1.70 (4H, m), 2.40–2.60 (6H, m), 3.05 (2H, t, J=5Hz), 3.20 (2H, q, J=8Hz), 3.88 (2H, t, J=5Hz), 6.12 (1H, s), 6.30 (1H, t, J=5Hz), 7.05 (1H, d, J=8Hz), 7.20–7.48 (5H, m), 7.76 (1H, d, J=8Hz), 9.02 (1H, s)

EXAMPLE 8

To a mixture of 7-amino-3-[4-(4-phenyl-1,2,3,6-tetrahydropyridin-1-yl)butyl]-1,2,3,4-tetrahydroquinazoline-2,4-dione (0.39 g), acetic acid (5 ml) and water (10 ml) was added a solution of potassium cyanate 0.16 g) in water (2 ml) and the resulting mixture was stirred for additional 3 hours. The reaction mixture was poured into water and precipitated solid was filtered, washed in turn with water and ethanol and dried to give 3-[4-(4-phenyl-1,2,3,6-tetrahydropyridin-1-yl)butyl]-7-ureido-1,2,3,4-tetrahydroquinazoline-2,4-dione (0.12 g).

mp : 260° C.

IR (Nujol) : 3420, 1700, 1640, 1550 cm$^{-1}$

NMR (DMSO-d$_6$, δ) : 1.52–1.75 (4H, m), 2.72 (2H, t, J=5Hz), 3.00–3.50 (4H, m), 3.72 (2H, t, J=5Hz), 3.92 (2H, t, J=5Hz), 6.18 (2H, s), 7.09 (1H, d, J=8Hz), 7.32–7.53 (5H, m), 7.75 (1H, d, J=8Hz), 9.34 (1H, s)

EXAMPLE 9

7-Methylsulfonylamino-3-[4-(4-phenyl-1,2,3,6-tetrahydropyridin-1-yl)butyl]-1,2,3,4-tetrahydroquinazoline-2,4-dione was obtained in substantially the same manner as that of Example 12.

mp : 213°–215° C.

IR (Nujol) : 3250, 1700, 1640, 1590 cm$^{-1}$

NMR (DMSO-d$_6$, δ) : 1.25–1.50 (4H, m), 2.20 (6H, t, J=5Hz), 2.42 (2H, t, J=5Hz), 2.72 (3H, s), 3.70 (2H, t, J=5Hz), 5.93 (1H, s), 6.33 (1H, s), 6.58 (1H, d, J=8Hz), 6.98–7.22 (5H, m), 7.55 (1H, d, J=8Hz), 7.65 (1H, s)

EXAMPLE 10

3-[4-(4-Phenyl-1,2,3,6-tetrahydropyridin-1-yl)butyl]--trifluoroacetamido-1,2,3,4-tetrahydroquinazoline-2,4-dione was obtained in substantially the same manner as that of Example 12.

mp : 245° C.

IR (Nujol) : 3220, 1720, 1690, 1630, 1560 cm$^{-1}$

NMR (DMSO-d$_6$, δ) : 1.40–1.70 (4H, m), 2.41 (4H, t, J=5Hz), 2.57 (2H, t, J=5Hz), 3.05 (2H, d, J=5Hz), 3.94 (2H, t, J=5Hz), 6.10 (1H, s), 7.17–7.43 (6H, m), 7.90 (1H, d, J=8Hz), 8.30 (1H, s)

EXAMPLE 11

6-Chloro-3-[4-(4-phenyl-1,2,3,6-tetrahydropyridin-1-yl)butyl]-1,2,3,4-tetrahydroquinazoline-2,4-dione was obtained in substantially the same manner as that of Example 1-1).

mp : 214°-222° C.

IR (Nujol) : 1700, 1640, 1590 cm$^{-1}$

NMR (CDCl$_3$, δ) : 1.65-1.85 (4H, m), 2.60-2.75 (4H, m), 2.85 (2H, t, J=5Hz), 3.30 (2H, d, J=1.5Hz), 4.10 (2H, t, J=5Hz), 6.00-6.10 (1H, m), 7.10 (1H, d, J=8.5Hz), 7.20-7.40 (5H, m), 7.50 (1H, dd, J=8.5Hz, 2.5Hz), 8.05 (1H, d, J=2.5Hz)

EXAMPLE 12

A mixture of 6-amino-3-[4-(4-phenyl-1,2,3,6-tetrahydropyridin-1-yl)butyl]-1,2,3,4-tetrahydroquinazoline-2,4-dione (390 mg), methanesulfonyl chloride (229 mg), potassium carbonate (276 mg) and dry N,N-dimethylformamide (10 ml) was stirred for 1 hour at room temperature. The mixture was poured into water, neutralized with 1N sodium hydroxide and extracted with ethyl acetate, and the extract was washed with brine. The organic layer was dried and evaporated. The crude residue was chromatographed on a silica gel (50 g), eluting with 10% methanol in dichloromethane to give 3-[4-(4-phenyl-1,2,3,6-tetrahydropyridin-1-yl)butyl]-6-methylsulfonylamino-1,2,3,4-tetrahydroquinazoline-2,4-dione (292 mg). Recrystallization from ethyl acetate gave a crystal thereof (202 mg).

mp : 193°-195° C.

IR (Nujol) : 3230, 1700, 1620, 1505, 1305, 1140, 975, 820, 740 cm$^{-1}$

NMR (DMSO-d$_6$, δ) : 1.40-1.70 (4H, m), 2.42 (4H, t, J=5Hz), 2.60 (2H, t, J=5Hz), 2.93 (3H, s), 3.06 (2H, d, J=5Hz), 3.92 (2H, t, J=5Hz), 6.14 (1H, s), 7.05-7.53 (7H, m), 7.78 (1H, s)

EXAMPLE 13

To a stirred solution of 3-[4-(4-phenyl-1,2,3,6-tetrahydropyridin-1-yl)butyl]-6-methylsulfonylamino-1,2,3,4-tetrahydroquinazoline-2,4-dione (158 mg) in methanol was added 10% hydrogen chloride in methanol solution (123 mg) at 5° C. After stirring for 1 hour at 5° C., the solution was evaporated. The residue was crystallized from isopropyl alcohol-ethyl acetate to give 3-[4-(4-phenyl-1,2,3,6-tetrahydropyridin-1-yl)butyl]-6-methylsulfonylamino-1,2,3,4-tetrahydroquinazoline-2,4-dione hydrochloride [81 mg].

mp : 115° C. (dec.)

IR (Nujol) : 1700, 1650, 1140, 970, 740 cm$^{-1}$

NMR (DMSO-d$_6$, δ) : 1.60-1.87 (4H, m), 2.80 (2H, t, J=5Hz), 2.93 (3H, s), 3.12-3.40 (6H, m), 3.93 (2H, t, J=5Hz), 6.20 (1H, s), 7.18-7.80 (8H, m), 9.87 (1H, s)

The following compounds (Examples 14-16) were obtained in substantially the same manner as that of Example 1-1).

EXAMPLE 14

7-Chloro-3-[4-(4-phenyl-1,2,3,6-tetrahydropyridin-1yl)butyl]-1,2,3,4-tetrahydroquinazoline-2,4-dione mp : 195°-197° C.

IR (Nujol) : 1720, 1650 cm$^{-1}$

NMR (CDCl$_3$, δ): 1.65-1.85 (4H, m), 2.60 (4H, m), 2.80 (2H, t, J=5Hz), 3.20 (2H, d, J=3Hz), 4.10 (2H, t, J-7Hz), 6.05-6.10 (1H, m), 7.10 (1H, d, J=1.5Hz), 7.20 (1H, dd, J=8Hz, 1.5Hz), 7.25-7.40 (5H, m), 8.05 (1H, d, J=8.5Hz)

EXAMPLE 15

3-[4-{4-(4-Methylphenyl)-1,2,3,6-tetrahydropyridin-1-yl}butyl]-1,2,3,4-tetrahydroquinazoline-2,4-dione mp : 190°-192° C.

IR (Nujol) : 1720, 1650 cm$^{-1}$

NMR (CDCl$_3$, δ) : 1.65-1.85 (4H, m), 2.30 (3H, s), 2.55-2.65 (4H, m), 2.25 (2H, t, J=5.5Hz), 3.15-3.25 (2H, m), 4.10 (2H, t, J=8Hz), 5.95-6.05 (1H, m), 7.05 (2H, d, J=7Hz), 7.15 (2H, d, J=7Hz), 7.20-7.30 (2H, m), 7.60 (1H, td, J=8Hz, 1Hz), 8.10 (1H, dd, J=8Hz, 1Hz), 9.50-9.70 (1H, br s)

EXAMPLE 16

3-[4-{4-(4-Fluorophenyl)-1,2,3,6-tetrahydropyridin-1-yl}butyl]-1,2,3,4-tetrahydroquinazoline-2,4-dione mp : 196°-198° C.

IR (Nujol) : 1710, 1650 cm$^{-1}$

NMR (CDCl$_3$, δ) : 1.60-1.90 (4H, m), 2.50-2.60 (4H, m), 2.75 (2H, t, J=6Hz), 3.15-3.25 (2H, m), 4.10 (2H, td, J=7.5Hz, 1Hz), 5.95-6.05 (1H, m), 6.95-7.10 (3H, m), 7.20-7.35 (3H, m), 7.60 (1H, td, J=7Hz, 1Hz), 8.10 (1H, dd, J=8Hz, 1.5Hz), 9.25-9.35 (1H, br s)

EXAMPLE 17

A mixture of 2-ethoxycarbonylamino-4-sulfamoyl-N-[4-4-phenyl-1,2,3,6-tetrahydropyridin-1-yl)butyl]benzamide (0.16 g), potassium hydroxide (54 mg) and ethanol (10 ml) was stirred under reflux for 4 hours. After evaporation of the solvent, a small amount of water was added and the solution was neutralized with 1N hydrochloric acid. The precipitated materials were collected, triturated with ethanol and recrystallized from ethanol to give crystals of 3-[4-4-phenyl-1,2,3,6-tetrahydropyridin-1-yl)butyl]-7-sulfamoyl-1,2,3,4-tetrahydroquinazoline-2,4-dione (63 mg).

mp : 213°-215° C.

IR (Nujol) : 1750, 1710, 1220, 1150 cm$^{-1}$

NMR (DMSO-d$_6$, δ) : 1.15 (3H, t, J=5Hz), 1.60-1.90 (4H, m), 2.65-3.00 (2H, m), 3.10-3.50 (4H, m), 3.55-4.10 (4H, m), 4.05 (2H, q, J=5Hz), 6.15-6.25 (1H, m), 7.30-7.50 (5H, m), 7.65 (1H, dd, J=7Hz, 1.5Hz), 7.80 (1H, s), 8.20 (1H, d, J=7Hz)

EXAMPLE 18

6-Nitro-3-[4-(4-phenyl-1,2,3,6-tetrahydropyridin-1-yl)butyl]-1,2,3,4-tetrahydroquinazoline-2,4-dione was obtained in substantially the same manner as that of Example 1-1).

mp : 184°-186° C.

IR (Nujol) : 1720, 1660, 1620, 1600 cm$^{-1}$

NMR (CDCl$_3$, δ) : 1.60-1.85 (4H, m), 2.55-2.65 (4H, m), 2.80 (2H, t, J=6Hz), 3.25 (2H, d, J=2.5Hz), 4.15 (2H, t, J=7.5Hz), 6.10 (1H, t, J=2.5Hz), 7.15-7 40 (6H, m), 8.40 (1H, dd, J=8Hz, 2.5Hz), 8.90 (1H, d, J=2.5Hz)

EXAMPLE 19

6-Amino-3-[4-(4-phenyl-1,2,3,6-tetrahydropyridin-1-yl)butyl]-1,2,3,4-tetrahydroquinazoline-2,4-dione was obtained in substantially the same manner as that of Example 3.

mp : 215° C. (dec.)

IR (Nujol) : 1710, 1640 cm$^{-1}$

NMR (CDCl$_3$OD, δ) : 1.60-1.80 (4H, m), 2.50-2.65 (4H, m), 2.75 (2H, t, J=5Hz), 3.20 (2H, d, J=2Hz), 4.05 (2H, d, J=7Hz), 6.05-6.10 (1H, m), 6.90-7.05 (2H, m), 7.25-7.40 (8H, m)

EXAMPLE 20

6-Hydroxyamino-3-[4-(4-phenyl-1,2,3,6-tetrahydropyridin-1-yl)butyl]-1,2,3,4-tetrahydroquinazoline-2,4-dione was obtained in substantially the same manner as that of Example 28.
mp : 234° C. (dec.)
IR (Nujol) : 1710, 1650, 1600 cm$^{-1}$

EXAMPLE 21

7-Methoxy-3-[4-(4-phenyl-1,2,3,6-tetrahydropyridin-1-yl)butyl]-1,2,3,4-tetrahydroquinazoline-2,4-dione was obtained in substantially the same manner as that of Example 1-1).
mp : 210°-212° C.
NMR (CDCl$_3$, δ) : 1.65-1.85 (4H, m), 2.55-2.65 (4H, m), 2.80 (2H, t, J=5Hz), 3.20-3.30 (2H, m), 3.85 (3H, s), 4.05-4.15 (2H, t, J=7Hz), 6.00-6.10 (1H, m), 6.50 (1H, d, J=2Hz), 6.75 (1H, dd, J=9Hz, 2Hz), 7.25-7.40 (5H, m), 8.00 (1H, d, J=9Hz), 9.70 (1H, br s)

EXAMPLE 22

A mixture of 7-methoxy-3-[4-[4-phenyl-1,2,3,6-tetrahydropyridin-1-yl)butyl]-1,2,3,4-tetrahydroquinazoline-2,4-dione (0.2 g), 47% hydrobromic acid (2.6 ml) and acetic acid (6 ml) was refluxed for 28 hours. After cooling, the reaction mixture was diluted with ethanol and the precipitated crystals were collected. Recrystallization from ethanol afforded 7-hydroxy-3-[4-(4-phenyl-1,2,3,6-tetrahydropyridin-1-yl)butyl]-1,2,3,4-tetrahydroquinazoline-2,4-dione hydrobromide (0.1 g).
mp : 278°-279° C.
IR (Nujol) : 3600-3300, 3300-3000, 1710, 1620 cm$^{-1}$
NMR (DMSO-d$_6$, δ): 1.55-1.85 (4H, m), 2.70-2.85 (2H, m), 3.15-3.40 (4H, m), 3.55-4.00 (4H, m), 6.15-6.25 (1H, br s), 6.55 (1H, d, J=1.5Hz), 6.60 (1H, dd, J=9Hz, 1.5Hz), 7.30-7.55 (5H, m), 7.75 (1H, d, J=9Hz), 9.50-9.70 (1H, br s)

The following compounds (Examples 23-25) were obtained in substantially the same manner as that of Example 1-1).

EXAMPLE 23

3-[4-(4-Phenyl-1,2,3,6-tetrahydropyridin-1--yl)butyl]-1,2,3,4-tetrahydroquinazoline-2,4-dione
mp : 186°-187° C.
IR (Nujol) : 1730, 1700, 1630 cm$^{-1}$
NMR (CDCl$_3$, δ) : 1.65-1.85 (4H, m), 2.55-2.65 (4H, m), 2.80 (2H, t, J=5Hz), 3.25 (2H, d, J=2.5Hz), 4.15 (2H, t, J=7Hz), 6.00-6.10 (1H, m), 7.10 (1H, d, J=8Hz), 7.15-7.40 (6H, m), 7.55-7.65 (1H, m), 8.10 (1H, dd, J=8Hz, 1.5Hz)

EXAMPLE 24

7-Methoxymethyl-3-[4-[4-phenyl-1,2,3,6-tetrahydropyridin-1-yl)butyl]-1,2,3,4-tetrahydroquinazoline-2,4-dione
mp : 194°-198° C.
IR (Nujol) 1705, 1645, 1595 cm$^{-1}$
NMR (DMSO-d$_6$, δ) : 1.55 (4H, m), 2.40 (4H, m), 2.60 (2H, m), 3.03 (2H, m), 3.30 (3H, s), 3.90 (2H, m), 4.49 (2H, s), 6.12 (1H, m), 7.10 (2H, m), 7.2-7.4 (5H, m), 7.90 (1H, d, J=8Hz)

EXAMPLE 25

7-Carbamoyl-3-[4-(4-phenyl-1,2,3,6-tetrahydropyridin-1-yl)butyl]-1,2,3,4-tetrahydroquinazoline-2,4-dione hydrochloride
mp : 273°-281° C.
IR (Nujol) : 3350, 3250, 1725, 1635, 1585 cm$^{-1}$
NMR (DMSO-d$_6$, δ) : 1.65 (4H, m), 2.75 (2H, m), 3.15 (2H, m), 3.5-4.0 (6H, m), 6.10 (1H, m), 7.1-7.7 (8H, m), 7.90 (1H, d, J=8Hz), 8.15 (1H, s), 10.30 (1H, br s)

EXAMPLE 26

A mixture of 7-carbamoyl-3-[4-(4-phenyl-1,2,3,6-tetrahydropyridin-1-yl)butyl]-1,2,3,4-tetrahydroquinazoline-2,4-dione (0.15 g), 1N sodium hydroxide solution (5 ml) and ethanol (5 ml) was stirred under reflux for 10 hours. After cooling, 1N hydrochloric acid (6 ml) was added and the precipitated crystals were collected to give 7-carboxy-3-[4-(4-phenyl-1,2,3,6-tetrahydropyridin-1-yl)butyl]-1,2,3,4-tetrahydroquinazoline-2,4-dione (0.15 g).
mp : 296°-305° C.
IR (Nujol) : 3250, 2700-2500, 1720, 1640 cm$^{-1}$
NMR (DMSO-d$_6$, δ) : 1.6-1.9 (4H, m), 2.80 (2H, m), 3.15 (4H, m), 3.80 (2H, m), 3.95 (2H, m), 6.15 (1H, m), 7.3-7.6 (5H, m), 7.70 (1H, dd, J=8Hz, 2Hz), 7.80 (1H, d, J=2Hz), 8.03 (1H, d, J=8Hz)

EXAMPLE 27

7-Morpholinocarbonyl-3-[4-(4-phenyl-1,2,3,6-tetrahydropyridin-1-yl)butyl]-1,2,3,4-tetrahydroquinazoline-2,4-dione was obtained in substantially the same manner as that of Example 1-1).
mp : 206°-210° C.
IR (Nujol) : 3200, 1715, 1645, 1625, 1600 cm$^{-1}$
NMR (CDCl$_3$, δ) : 1.75 (4H, m), 2.65 (4H, m), 2.85 (2H, m), 3.30 (2H, m), 3.45 (2H, m), 3.65 (2H, m), 3.80 (4H, m), 4.10 (2H, m), 6.05 (1H, m), 7.1-7.4 (7H, m), 8.12 (1H, d, J=8Hz)

EXAMPLE 28

To a stirred solution of 7-nitro-3-[4-(4-phenyl-1,2,3,6-tetrahydropyridin-1-yl)butyl]-1,2,3,4-tetrahydroquinazoline-2,4-dione (2.1 g) in 50% aqueous tetrahydrofuran (210 ml) was added ammonium chloride (2.68 g) in water (27 ml). To this mixture was added zinc dust (1.65 g) by five portions over a period of 3 hours. The temperature was raised at 32° C. during the reaction. After additional stirring for 2 hours, the precipitated materials were filtered, washed with water and extracted with dimethylformamide (100 ml) under nitrogen. The organic extract was filtered and the filtered cake was washed with dimethylformamide (20 ml). The combined organic solution was diluted with water (24 ml), cooled in a refrigerator, and then treated with active charcoal (1.05 g) and silica gel (2.1 g). The charcoal and silica gel were filtered off and washed with 80% aqueous dimethylformamide (5 ml). To the combined solution was added dropwise cold water (96 ml) with stirring on an ice bath and the precipitated crystals were collected, washed with water, and then suspended in methanol (50 ml). To this mixture was added 10% hydrogen chloride in methanol (50 ml) and the mixture was stirred for 1 hour. The precipitated crystals were collected, washed with methanol, stirred with water, and then filtered and dried to give 7-hydroxyamino-3-[4-(4-phenyl-1,2,3,6-tetrahydropyridin-1-yl)butyl]-1,2,3,4-tetrahydroquinazoline-2,4-dione (0.60 g).
mp : 265°-270° C.

EXAMPLE 29

7-Morpholinomethyl-3-[4-(4-phenyl-1,2,3,6-tetrahydropyridin-1-yl)butyl]-1,2,3,4-tetrahydroquinazoline- 2,4-dione was obtained in substantially the same manner as that of Example 1-1).

mp : 154°–156° C.

IR (Nujol) : 1710, 1640, 1595 cm$^{-1}$

NMR (DMSO-d$_6$, δ) : 1.55 (4H, m), 2.40 (8H, m), 2.60 (2H, m), 3.05 (2H, m), 3.52 (2H, s), 3.60 (4H, m), 3.92 (2H, m), 6.15 (1H, m), q 7.15 (2H, m), 7.2–7.45 (5H, m), 7.90 (1H, d, J=8Hz)

EXAMPLE 30

6-Methoxycarbonyl-3-[4-(4-phenyl-1,2,3,6-tetrahydropyridin-1-yl)butyl]-1,2,3,4-tetrahydroquinazoline-2,4-dione was obtained in substantially the same manner as that of Example 1-1).

mp : 138° C.

EXAMPLE 31

6-Carboxy-3-[4-(4-phenyl-1,2,3,6-tetrahydropyridin-1-yl)butyl]-1,2,3,4-tetrahydroquinazoline-2,4-dione was obtained in substantially the same manner as that of Example 26.

mp : 237° C.

NMR (DMSO-d$_6$, δ) : 1.68 (4H, br, s), 2.69 (2H, br s), 3.32 (6H, m), 3.95 (2H, t, J=7Hz), 6.17 (1H, t, J=4Hz), 7.27 (1H, d, J=9Hz), 7.31 (1H, d, J=8Hz), 7.37 (2H, t, J=8Hz), 7.47 (2H, d, J=8Hz), 8.16 (1H, dd, J=2Hz, 9Hz), 8.49 (1H, d, J=2Hz), 11.78 (1H, s)

EXAMPLE 32

6-Ethylsulfonylamino-3-[4-(4-phenyl-1,2,3,6-tetrahydropyridin-1-yl)butyl]-1,2,3,4-tetrahydroquinazoline-2,4-dione was obtained in substantially the same manner as that of Example 12.

mp : 210° C. (dec.)

IR (Nujol) : 3250, 1705, 1620, 1505, 1310, 1140 cm$^{-1}$

NMR (DMSO-d$_6$, δ) : 1.20 (3H, t, J=8Hz), 1.47–1.70 (4H, m), 2.40–2.50 (4H, m), 2.62 (2H, d, J=5Hz), 3.05 (2H, q, J=8Hz), 3.09 (2H, d, J=5Hz), 3.92 (2H, t, J=5Hz), 6.14 (1H, br s), 7.14–7.57 (7H, m), 7.80 (1H, s)

EXAMPLE 33

3-[4-(4-phenyl-1,2,3,6-tetrahydropyridin-1-yl)butyl]-1,2,3,4-tetrahydroquinazoline-2,4-dione was obtained in substantially the same manner as that of Example 1-1).

NMR (CDCl$_3$, δ) : 1.70 (4H, m), 2.57 (4H, m), 2.72 (2H, m), 3.16 (2H, m), 4.10 (2H, m), 4.27 (2H, s), 6.01 (1H, m), 7.0–7.5 (21H, m), 7.71 (1H, s), 8.03 (1H, d, J=8Hz), 8.19 (1H, s)

EXAMPLES 34

A solution of 3-[4-(4-phenyl-1,2,3,6-tetrahydropyridin-1-yl)butyl]-1,2,3,4-tetrahydroquinazoline-2,4-dione (1.1 g) and trifluoroacetic acid (10 ml) in dry methylene chloride (10 ml) stirred at room temperature overnight. After evaporation of the solvent, the crude residue was taken up with ethyl acetate, washed with saturated sodium bicarbonate solution, dried over magnesium sulfate and evaporated to give a solid, which was chromatographed on a silica gel [elution with a mixed solvent of chloroform and methanol (20:1)] to afford crystals (0.53 g). Recrystallization of the crystals from ethanol gave 7-hydroxymethyl-3-[4-(4-phenyl-1,2,3,6-tetrahydropyridin-1-yl)butyl]-1,2,3,4-tetrahydroquinazoline-2,4-dione (0.16 g).

mp : 224°–226° C.

IR (Nujol) : 3250, 1700, 1620 cm$^{-1}$

NMR (DMSO-d$_6$, δ): 1.60 (4H, m), 2.43 (4H, m), 2.60 (2H, m), 3.07 (2H, m), 3.92 (2H, m), 4.58 (2H, d, J=7Hz), 5.48 (1H, t, J=7Hz), 6.15 (1H, m), 7.1–7.5 (7H, m), 7.89 (1H, d, J=8Hz)

EXAMPLE 35

7-Hydroxyamino-3-[4-(4-phenyl-1,2,3,6-tetrahydropyridin-1-yl)butyl]-1,2,3,4-tetrahydroquinazoline-2,4-dione was obtained in substantially the same manner as that of Example 1-1) or Example 17.

mp : 187°–189° C.

IR (Nujol) : 3250, 1700 cm$^{-1}$

NMR (DMSO-d$_6$, δ) : 1.42–1.68 (4H, m), 2.38–2.52 (4H, m), 2.60 (2H, t, J=5Hz), 3.05 (2H, d, J=5Hz), 3.88 (2H, t, J=5Hz), 6.10–6.15 (1H, m), 6.51 (1H, d, J=8Hz), 6.54 (1H, s), 7.30–7.45 (6H, m), 7.65 (1H, d, J=8Hz), 8.75 (1H, s), 9.15 (1H, s)

EXAMPLE 36

3-[4-[4-Phenyl-1,2,3,6-tetrahydropyridin-1-yl)butyl]-6-methylsulfonylamino-1,2,3,4-tetrahydroquinazoline-2,4-dione was obtained in substantially the same manner as that of Example 1-1) or Example 17.

mp : 193°–195° C.

IR (Nujol) : 3230, 1700, 1620, 1505, 1305, 1140, 975, 820, 740 cm$^{-1}$

NMR (DMSO-d$_6$, δ) : 1.40–1.70 (4H, m), 2.42 (4H, t, J=5Hz), 2.60 (2H, t, J=5Hz), 2.93 (3H, s), 3.06 (2H, d, J=5Hz), 3.92 (2H, t, J=5Hz), 6.14 (1H), s), 7.05–7.53 (7H, m), 7.78 (1H, s)

What we claim is:

1. A compound of the formula:

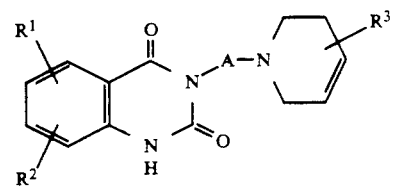

in which

R$^1$ and R$^2$ are each hydrogen, halogen, nitro, amino, ureido, N'-(lower) alkylureido, lower alkylsulfonylamino, protected amino, hydroxyamino, lower alkyl, hydroxy, protected hydroxy, sulfamoyl, carboxy, protected carboxy, mercapto, lower alkylthio, hydroxy(lower) alkyl or protected hydroxy(lower) alkyl, morpholinocarbonyl or morpholino(lower) alkyl;

R$^3$ is aryl which may have suitable substituent(s), and

A is lower alkylene, or pharmaceutically acceptable salts thereof.

2. A compound according to claim 1, wherein said protected carboxy group is selected from the group consisting of carbamoyl and lower alkoxycarbonyl, said protected amino group is selected from the group consisting of lower alkanoyl, trihalo(lower)alkanoyl, lower alkoxycarbonyl, carbamoyl, N-(lower)alkylcarbamoyl and lower alkylsulfonyl, said protected hydroxy group is selected from the group consisting of lower alkyl, acyl, and ar(lower)alkyl, and wherein said protected hydroxy(lower)alkyl is selected from the group consisting of lower alkoxy(lower)alkyl and triphenyl(lower)alkoxy(lower)alkyl.

3. The compound of claim 1, wherein

R$^1$ and R$^2$ are each hydrogen, halogen, nitro, amino, ureido, N'-(lower)-alkylureido, lower alkylsulfonylamino, acylamino, hydoxyamino, lower alkoxy, lower alkyl, hydroxy, sulfamoyl, carboxy, esterified carboxy, carbamoyl, mercapto, morpholinocarbonyl, morpholino(lower)alkyl, lower alkylthio, hydroxy(lower)alkyl, lower alkoxy(lower)alkyl or triphenyl(lower)alkoxy(lower)alkyl, and R³ is phenyl which is unsubstituted or substituted by a group consisting of halogen and lower alkyl.

4. The compound of claim 3, wherein

R¹ and R² are each hydrogen, halogen, nitro, amino, lower alkanoylamino, hydroxyamino, trihalo(lower)alkanoylamino, lower alkoxycarbonylamino, ureido, N'-(lower)alkylureido, lower alkylsulfonylamino, lower alkoxy, lower alkyl, hydroxy, sulfamoyl, carboxy, lower alkoxycarbonyl, carbamoyl, mercapto, morpholinocarbonyl, morpholino(lower)alkyl, lower alkylthio, hydroxy(lower)alkyl or protected hydroxy(lower)alkyl, and R³ is phenyl which is unsubstituted or substituted by a group consisting of halogen and lower alkyl.

5. The compound of claim 4, wherein

R¹ and R² are each hydrogen, halogen, nitro, amino, C₁–C₄ alkanoylamino, trihalo(C₁–C₄)alkanoylamino, hydroxyamino, C₁–C₄-alkoxycarbonylamino, ureido, N'-(C₁–C₄)-alkylureido, C₁–C₄ alkylsulfonylamino, C₁–C₄ alkoxy, C₁–C₄ alkyl, hydroxy, sulfamoyl, carboxy, C₁–C₄ alkoxycarbonyl, carbamoyl, mercapto, morpholinocarbonyl, morpholino(C₁–C₄)alkyl, C₁–C₄ alkylthio, hydroxy(C₁–C₄)alkyl, C₁–C₄ alkoxy(C₁–C₄)alkyl or triphenyl(C₁–C₄)alkoxy(C₁–C₄)alkyl, R³ is phenyl which is unsubstituted or substituted by a group consisting of halogen and C₁–C₄ alkyl, and A is C₁–C₆ alkylene.

6. The compound of claim 5, wherein

R¹ and R² are each hydrogen, halogen, nitro, amino, acetamido, trifluoroacetamido, ethoxycarbonylamino, ureido, N'-ethylureido, methylsulfonylamino, ethylsulfonylamino, methoxy, hydroxy, sulfamoyl, carboxy, hydroxyamino, carbamoyl, morpholinocarbonyl, morpholinomethyl, hydroxymethyl, methoxymethyl or trityloxymethyl, R³ is phenyl, 4-tolyl or 4-fluorophenyl, and A is tetramethylene.

7. A compound according to claim 1, in which R¹ and R² are each hydrogen, halogen, nitro, amino, ureido, N'-(lower)alkylureido, lower alkylsulfonylamino, hydoxyamino, lower alkoxy, hydroxy, sulfamoyl, carboxy, mercapto, lower alkylthio, hydroxy(lower)alkyl, morpholinocarbonyl or morpholino(lower)alkyl; and R³ is aryl which may be substituted by one or more substitutents selected from the group consisting of fluorine, chlorine, bromine, iodine and lower alkyl.

8. A compound of claim 6, which is selected from the group consisting of 3-[4-(4-phenyl-1,2,3,6-tetrahydropyridin-1-yl)butyl]-6-methylsulfonylamino-1,2,3,4-tetrahydroquinazoline-2,4-dione and 7-hydroxyamino-3-[4-(4-phenyl-1,2,3,6-tetrahydropyridin-1-yl)butyl]-1,2,3,4-tetrahydroquinazoline-2,4-dione.

9. A compound of the formula:

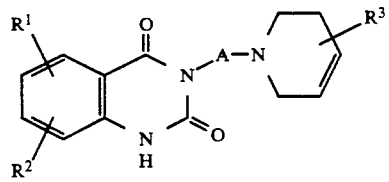

in which

R¹ is hydrogen,

R² is lower alkylsulfonylamino

R³ is phenyl, and

A is lower alkylene, or pharmaceutically acceptable salts thereof.

10. A compound, which is 6-ethylsulfonylamino-3-[4-(4-phenyl-1,2,3,6-tetrahydropyridin-1-yl)butyl]-1,2,3,4-tetrahydroquinazoline-2,4-dione or its acid addition salt.

11. A compound according to claim 1, which is 6-Chloro-3-[4-(4-phenyl-1,2,3,6-tetrahydropyridin-1-yl)butyl]-1,2,3,4-tetrahydroquinazoline-2,4-dione.

12. A dopamine receptor agonist, 5-HT receptor antagonist and α₁-receptor antagonist pharmaceutical composition comprising, as an active ingredient, an effective amount of a compound of claim 1 in admixture with a pharmaceutically acceptable carrier or excipient.

13. A method for the treatment of dopamine receptor mediated diseases, 5-HT receptor mediated diseases or α₁ receptor mediated diseases which comprises administering an effective amount of a compound of claim 12 to a human being or animal.

* * * * *